(12) United States Patent
Goettsche et al.

(10) Patent No.: US 6,352,583 B1
(45) Date of Patent: Mar. 5, 2002

(54) WOOD PRESERVATIVE FOR SUBSEQUENT APPLICATION

(75) Inventors: Reimer Goettsche, Baden-Baden; Wendelin Hettler; Michael Breuer, both of Sinzheim; Hans-Peter Seelmann-Eggebert, Limburgerhof, all of (DE)

(73) Assignee: Dr. Wolman GmbH, Sinzheim (DE)

( * ) Notice: Subject to any disclaimer, the term of this patent is extended or adjusted under 35 U.S.C. 154(b) by 0 days.

(21) Appl. No.: 09/380,373

(22) PCT Filed: Feb. 23, 1998

(86) PCT No.: PCT/EP98/01035

§ 371 Date: Sep. 1, 1999

§ 102(e) Date: Sep. 1, 1999

(87) PCT Pub. No.: WO98/39146

PCT Pub. Date: Sep. 11, 1998

(30) Foreign Application Priority Data

Mar. 5, 1997 (DE) .......................... 197 09 116

(51) Int. Cl.⁷ .............................. B27K 3/50; B27K 3/52; A01N 59/20
(52) U.S. Cl. ................ 106/18.32; 106/18.3; 106/18.31; 424/404; 424/405; 424/638; 514/557; 514/561; 514/574
(58) Field of Search ................ 106/18.32, 18.3, 106/18.31; 424/638, 404, 405; 514/557, 561, 574

(56) References Cited

U.S. PATENT DOCUMENTS

| | | | | |
|---|---|---|---|---|
| 4,761,179 A | * | 8/1988 | Goettsche et al. | 106/18.32 |
| 4,808,407 A | * | 2/1989 | Hein et al. | 424/633 |
| 4,857,322 A | * | 8/1989 | Goettsche et al. | 424/633 |
| 4,906,660 A | * | 3/1990 | West | 514/499 |
| 5,078,912 A | * | 1/1992 | Goettsche et al. | 252/400.53 |
| 5,187,194 A | * | 2/1993 | Goettsche et al. | 514/499 |
| 5,342,438 A | | 8/1994 | West | 106/18.3 |
| 5,853,766 A | * | 12/1998 | Goettsche et al. | 424/632 |
| 5,874,025 A | * | 2/1999 | Heuer et al. | 252/383 |
| 6,110,263 A | * | 8/2000 | Goettsche et al. | 106/18.32 |

FOREIGN PATENT DOCUMENTS

| | | | |
|---|---|---|---|
| AU | 35 221/78 | | 10/1979 |
| DE | 3743821 | * | 7/1989 |
| DE | 38 35 370 | | 4/1990 |
| DE | 196 08 435 | * | 9/1997 |
| EP | 238051 | * | 9/1987 |
| WO | 96/23635 | | 8/1996 |
| WO | 96/23636 | | 8/1996 |

* cited by examiner

*Primary Examiner*—Anthony Green
(74) *Attorney, Agent, or Firm*—Keil & Weinkauf

(57) ABSTRACT

Use of a wood preservative for the supplemental protection of wood, comprising a copper compound, an alkanolmonoamine and a complexing organic carboxylic acid or its ammonium or alkali metal salts, and a wrap for the supplemental protection of wood which comprises this wood preservative.

19 Claims, No Drawings

WOOD PRESERVATIVE FOR SUBSEQUENT APPLICATION

The present invention relates to the use of a wood preservative for the supplemental protection of wood, comprising a copper compound, an alkanolmonoamine and a complexing organic carboxylic acid or its ammonium or alkali metal salts and a wrap for the supplemental protection of wood which contains this wood preservative.

For the supplemental maintenance of transmission poles existing in the grid of telephone and electricity-supplying companies, or similar poles, wraps with water-soluble wood preservatives are applied in particular in the groundline region. It is known to employ, for this purpose, water-soluble salts based on inorganic fluorine compounds, e.g. alkali metal fluorides, in some cases together with alkali metal bichromate or boron compounds such as boric acid or borax. However, these salts act exclusively against wood-destroying Basidiomycetes, while not providing an activity against soft rot for applications which involve contact with the soil. Substances which have been proposed as active against soft rot are, on the one hand, dinitrophenol (Barry A. Richardson: Wood preservation—The Construction Press Ltd., Lancaster p. 181) or combinations of the abovementioned compounds with water-soluble copper salts, e.g. copper sulfate or copper acetate. Mixtures of copper sulfate, also in combination with alkali bichromate, with boric acid and copper acetate with alkali fluoroborates are part of the prior art. In the meantime, dinitrophenol has been excluded due to its toxicity.

The water-soluble abovementioned copper compounds, alone, but also in the abovementioned combinations, do not have good diffusion properties for sufficiently penetrating for example the sapwood of pine poles, also during long standing times, and to reach the heart.

Wood preservatives based on copper and amines as complexing agent have been proposed for large-scale impregnation, in particular boiler pressure impregnation.

EP-B-211 181 relates to a wood preservative based on a copper salt and monoethanolamine for the boiler pressure impregnation of wood.

EP-B 270 848 describes a wood preservative based on a copper compound, a carboxylic acid and an aliphatic polyamine for boiler pressure impregnation.

EP-A 423 674 describes a wood preservative based on a metal salt of an N-organyldiazeniumdioxy compound and a complexing polymeric amine for the boiler pressure method.

All the above-described wood preservatives feature high copper fixation potential in the wood. This limits the diffusibility of the copper, which is why these systems are not suitable for the supplemental protection of wood.

"Known, currently used systems for the supplemental protection of wood contain, for example, combinations of copper naphthanate, boron compounds and fluorine compounds. An example of this product type which is used mainly in the USA is CuRAP 20 (ISK Biotech), a paste containing 18.16% of amine-based copper naphthenate and 40% of sodium tetraborate decahydrate. Analyses on poles (wood species: Douglas-fir and pine), which have been treated with this product, showed that, after 1 to 3 years of application, most of the copper is distributed virtually only in the outer zone (0–10 mm) in the wood (depth of penetration analyzed: up to 25 mm) and these products thus only have a very limited diffusibility as regards copper (Conserving energy by environmentally acceptable practices in maintaining and procuring transmission poles. 15th annual report, September 1995, J. J. Morrell, Oregon State University, Corvallis, Oreg.)."

WO 96/23636 describes wood preservatives in paste form which comprise a fungicidal metal compound and a fungicidal boron compound. The metal compounds also embrace copper complexed with aminocarboxylic acids or polycarboxylic acids.

WO 96/23635 describes a wood preservative which comprises a metal chelate. Described are copper complexes with amino acids, iminodiacetic acid, ethylenediaminotetraacetic acid, dicarboxylic acids and polyphosphates.

The copper complexes with nitrogen-containing complexing polycarboxylic acids, e.g. imidodiacetic acid, ethylenediaminotetraacetic acid or nitrilotriacetic acid, do not become fixed in wood, but are leached completely from the wood (WO 96/23635, page 20, Table 6) and thus diffuse from wood into the environment when exposed to moisture (weathering, contact with the soil), which not only means increased pollution, but, as time goes by, the wood is not protected sufficiently against soft rot. This also applies to other complexing acids such as the hydroxycarboxylic acids, e.g. citric acid, malic acid and tartaric acid.

In contrast, copper chelates with other dicarboxylic acids, for example phthalic acid, maleic acids, lack sufficient diffusibility.

Thus, formulations based on the abovementioned substances alone are not ideally suited for the supplemental protection of wood.

German Patent Application DE-A 196 08 435 describes the use of a wood preservative for the supplemental protection of wood which comprises a copper compound, a polyamine and an inorganic fungicide.

It is an object of the present invention to provide a wood preservative for the supplemental protection of wood which features good diffusibility of the copper in the wood combined with good protection against soft rot and Basidiomycetes.

It is a further object of the present invention to provide a wrap which comprises this wood preservative for the supplemental protection of wood.

We have found that these objects are achieved by a wood preservative, for the supplemental protection of wood, based on a copper compound, an alkanolmonoamine and a complexing organic carboxylic acid or its ammonium or alkali metal salts and, if appropriate, further auxiliaries and, if appropriate, water.

For the sake of simplicity, all or some of the copper compound may also be present in the form of the salt of the complexing organic carboxylic acid (e.g. copper citrate, copper tartrate).

To improve the activity, inorganic fungicides may also be admixed to the wood preservative as a complement.

These wood preservatives are especially suitable for the supplemental protection and supplemental maintenance of wood and are used in the form of wraps and by the injection inoculation-method, the drilled hole method and the paste method. In the presence of moisture, e.g. ground contact, they penetrate the sapwood, and they have a good depth action.

Copper compounds which can be used are compounds which are soluble or insoluble in water, e.g. copper sulfate, copper acetate, copper citrate, copper tartrate, copper naphthenate, copper hydroxide, copper hydroxycarbonate, copper oxychloride, copper oxide, copper borate, copper fluoride, copper fluoroborate, bis(N-cyclohexyldiazeniumdioxy)copper, or mixtures of these.

Preferred are copper hydroxycarbonate, copper hydroxide and mixtures of these.

Copper hydroxide, specifically stabilized copper hydroxide (Norddeutsche Affinerie), is especially preferably used.

The activity of the wood preservatives can be improved by the salts of N-cyclohexyldiazenium dioxide and other diazenium dioxides, e.g. as the potassium salt, in which case, as a rule, the abovementioned bis(N-cyclohexyldiazeniumdioxy)copper is formed with copper compounds.

The mixtures comprise from 0.25 to 15% by weight of copper, calculated as the element. Some of the copper can also be replaced, for example by a corresponding zinc compound.

The following can be used as alkanolmonoamines: monoalkanolmonoamines, dialkanolmonoamines, trialkanolmonoamines having 2 to 18 C atoms, and N—$C_1$–$C_4$-monoalkylmonoalkanolmonoamines, N—$C_1$–$C_4$-dialkylmonoalkanolmonoamines, N—$C_1$–$C_4$-monoalkyldialkanolmonoamines and mixtures of these.

Suitable examples are: monoethanolamine, diethanolamine, triethanolamine, 3-aminopropanol, monoisopropanolamine, 4-aminobutanol, monomethylethanolamine, dimethylethanolamine, triethylethanolamine, monoethylethanolamine, N-methyldiethanolamine and mixtures of these.

The following are preferably used: monoethanolamine, diethanolamine, triethanolamine, isopropanolamine, and mixtures of these.

Monoethanolamine is especially preferably used.

Examples of complexing organic carboxylic acids which are used are hydroxycarboxylic acids, aminocarboxylic acids, nitrogen-containing polycarboxylic acids, the ammonium or alkali metal salts of these, and mixtures of these.

Examples of suitable hydroxycarboxylic acids which can be used are glycolic acid, lactic acid, tartaric acid, citric acid, malic acid, their ammonium or alkali metal salts, and mixtures of these.

Amino acids, e.g. glycine, sarcosine, the ammonium or alkali metal salts of these and mixtures of these may also be used.

Examples of suitable nitrogen-containing complexing polycarboxylic acids which can be used are nitrilotriacetic acid (NTA), ethylenediaminetetraacetic acid (EDTA), diethylenetriaminepentaacetic acid (DPTA), propylenediaminetetraacetic acid (PDTA), hydroxyethylethylenediaminetriacetic acid (HEDTA), β-alaninediacetic acid, the ammonium or alkali metal salts of these and mixtures of these.

Hydroxycarboxylic acids are preferably used, because they are environmentally friendly. Citric acid is especially preferred in this context.

Suitable inorganic fungicides are boron compounds such as alkali metal borates, aminoborates, boric acid, boric esters and $B_2O_3$; fluorides such as alkali metal fluorides, alkali metal bifluorides, silicon fluorides, ammonium fluorides, ammonium hydrogen fluorides; fluoroborates, fluorophosphates, difluorophosphates, and mixtures of these.

The following are preferred: sodium fluoroborate, potassium fluoroborate, boric acid, sodium fluoride and mixtures of these.

The wood preservatives of the present invention can additionally comprise auxiliaries such as water, binders, paste formers, organic and inorganic bases, aliphatic carboxylic acids, the ammonium or alkali metal salts of these, plasticizers, fillers, wetters, thickeners and mixtures of these.

The wood preservatives may additionally comprise water for modifying the viscosity and for handling.

Examples of substances which can be used as binders and paste formers are acrylate resins in the form of aqueous dispersions or powders; plastisols, aminoplasts, phenoplasts, PVC with plasticizers, and mixtures of these.

Organic and inorganic bases which can be used are ammonia, alkali metal hydroxide solution, amines, or mixtures of these. Examples of suitable amines are mono-, di- and trialkylamines, and also poyamines.

The following may additionally be used for improving the flexibility of the wood preservative dried onto a support material: aliphatic $C_5$–$C_{20}$-carboxylic acids such as hexanoic acid, heptanoic acid, octanoic acid, nonanoic acid, decanoic acid, 2-ethylenepentanoic acid, 2-ethylhexanoic acid, 2-ethylheptanoic acid, isooctanoic acid, isononanoic acid, isodecanoic acid, versatic acids (highly branched monocarboxylic acids), dicarboxylic acids ($C_5$–$C_{20}$), e.g. decanedicarboxylic acid, sebacic acid. Also suitable are polycarboxylic acids such as polyacrylic acids or copolymers of acrylic acid and, for example, maleic acid and naphtenic [sic] acid.

Suitable wood preservatives comprise, for example,
 2–50% by weight, preferably 5–40% by weight, of a copper compound,
 2–60% by weight, preferably 5–50% by weight, of an alkanolmonoamine,
 1–65% by weight, preferably 2–55% by weight of a complexing organic carboxylic acid or an ammonium or alkali metal salt thereof,
 0–50% by weight, preferably 5–50% by weight of an inorganic fungicide,
 0–25% by weight, preferably 1–20% by weight of an alkali metal salt of N-cyclohexyldiazenium dioxide,
 0–25% by weight, preferably 1–20% by weight of an auxiliary,
 0–50% by weight, preferably 1–40% by weight of water,
the total of all components being 100% by weight.

The following wood preservatives have proven themselves:
 a) 5–40% by weight of a copper compound,
 5–60% by weight of an alkanolamine,
 5–35% by weight of a complexing organic carboxylic acid,
 5–50% by weight of an inorganic fungicide,
 2.5–50% by weight of water,
or, specifically when using binders and paste formers,
 a) 5–40% by weight of a copper compound,
 5–60% by weight of an alkanolamine,
 5–35% by weight of a complexing organic carboxylic acid,
 5–50% by weight of an inorganic fungicide,
 0–5% by weight of an alkali metal salt of N-cyclohexyldiazenium dioxyl [sic],
 5–40% by weight of an auxiliary,
 0–30% by weight of water.

The wood preservatives, which may be present in the form of concentrates or, diluted with water, as viscous solutions or in the form of pastes, if appropriate also as solid salts, are best prepared by dissolving an alkanolmonoamine and a complexing organic carboxylic acid, if appropriate using water and/or auxiliaries, and treating the stirred solution with the copper compound.

The copper compounds then dissolve in this mixture, forming complexes.

This premix may already exist in the form of a highly concentrated paste to which the inorganic fungicides and, if appropriate, other auxiliaries are then added, with stirring.

The residual fixation of the copper can be adapted to the use conditions by altering the alkanolamine/acid ratio.

The pH of the wood preservative in the form of the concentrate or paste is generally from pH 7–12. The concentrates or pastes can be applied to or incorporated into a suitable support material either directly or with the addition of a binder, depending on the purpose in question. Examples of suitable support materials are polymer films or formed fabrics, e.g. made of glass fiber, polypropylene, polyester fiber, viscose fiber, foam plastics or other porous polymer compositions. The concentrates are applied to the support material for example by rolling (calendering). Examples of substances which may be used as binders are acrylate resins in the forms of aqueous dispersions, powders; plastisols, aminoplasts, phenoplasts, PVC with plasticizers.

In most cases, the concentrate/support system is subsequently dried, for example in the air or, for example in an oven at from approximately 100 to 180° C., the concentrate drying to a highly viscous consistency and being bound to the support; if appropriate, this binding can be improved by the addition of the abovementioned binders; if necessary, this can simultaneously reduce the release of wood preservative after application if the binder is employed at high dosage rates.

The concentrates, in particular when adding binders, may also be extruded, dried and cut to size in order to obtain salt cartridges for insertion into wood via drilled holes, for example when using the drilled hole method. Also, it is possible to make cartridges of pulverulent mixtures, for example when using spray-dried concentrates or when using pulverulent raw materials in the form of pressed articles consisting of salt.

The diffusible pastes and concentrates or cartridges can be applied in the various processes of supplemental protection and supplemental maintenance, when the aim is to achieve larger amounts of protectant introduced and deeper penetration depth in the case of wooden components which are particularly at risk.

The pastes are suitable for the wrap method, such as single wraps or multiple wraps, the injection inoculation method, the drilled hole method and the paste method.

Application is carried out in the form of preventive or else curative protective treatments for the following purposes:

a) to impart long-term protection to certain sections of timber which is otherwise not treated with wood preservatives, e.g. ceiling beam heads;

b) to increase, in the danger zones, the amounts introduced or penetration depth achieved by the initial treatment;

c) to supplement or increase the protectant content of the basic protection in wood already used in existing constructions after prolonged standing time (time of use);

d) to reach, in wooden components used in existing constructions, even those zones which cannot be reached with customary soaking methods, in particular when carrying out a curative measure.

The invention is described with reference to the following examples:

For the experiments, defined amounts of the pastes/concentrates were applied to foamed material as support. The foamed material together with the paste then underwent a drying process. The resulting wrap was applied, after preparation, to buried round timber of pine wood in the groundline region. This region was subsequently wrapped with a self-adhesive PVC film and thus protected against penetration of water from the outside.

After a standing time of 12 months, the round timber was dug out, cut at right angles to the grain in the zone of the groundline region, the round timber shells [sic] were removed, and copper penetration was determined by allowing them to react (spraying) with a 0.2% strength aqueous solution of the monosodium salt of 4-(pyrid-2-ylazo) resorcinol (reagent for copper).

The round pine timber used for the experiments had a diameter of at least 20 cm and sapwood thicknesses of $\geq 3$ cm. An amount of approx. 500 g of concentrate/salt mixture was applied to each wrap, and the support material together with the concentrate of the active ingredient was incorporated in such a way that it was located approximately 10 cm above ground level and approximately 30 cm below ground level; the film cover overlapped this zone by in each case at least 10 cm. The wrap dimension was 40 cm×80 cm. At least two wraps were applied to different round timbers for each formulation and tested for penetration behavior.

EXAMPLE A (not according to the invention)

35% of copper sulfate
32% of potassium bichromate
30% of boric acid
3% of sodium hydrogen sulfate The salt was ground and made into a paste with water, acrylate dispersion (50% aqueous dispersion of a copolymer of n-butyl acrylate and styrene) as binder (10 parts of concentrate/2 parts of water/3 parts of binder), and the paste was applied to the foamed material as support and dried continuously for at least 15 minutes at 120° C.

The resulting wraps were applied to round timber. After a standing time of 12 months, the timber was removed, cut open, and the copper penetration was determined.

| Copper penetration after a standing time of 12 months | | |
|---|---|---|
| Round timber 1a: | average sapwood thickness: | approx. 35 mm |
| | average copper penetration: | approx. 9 mm |
| | At no point was the heart reached | |
| Round timber 2a: | average sapwood thickness: | approx. 38 mm |
| | average copper penetration: | approx. 12 mm |
| | At no point was the heart reached | |

EXAMPLE B (not according to the invention)

50% of copper sulfate
45% of boric acid
5% of sodium hydrogen sulfate

After the salt has been ground, it was made into a paste with water, acrylate dispersion (50% aqueous dispersion of a copolymer of n-butyl acrylate and styrene) as binder (10 parts of concentrate/2 parts of water/3 parts of binder), applied to the foamed material and dried for at least 24 hours at room temperature. The wraps were applied.

| Copper penetration after a standing time of 12 months | | |
|---|---|---|
| Round timber 1b: | average sapwood thickness: | approx. 41 mm |
| | average copper penetration: | approx. 7 mm |
| | At no point was the heart reached | |

-continued

| Copper penetration after a standing time of 12 months | | |
| --- | --- | --- |
| Round timber 2b: | average sapwood thickness: | approx. 37 mm |
| | average copper penetration: | approx. 9 mm |
| | At no point was the heart reached | |

EXAMPLE C (not according to the invention)

50% of copper sulfate
50% of sodium fluoroborate

After the salt has been ground, it was made into a paste with water, acrylate dispersion (50% aqueous dispersion of a copolymer of n-butyl acrylate and styrene) as binder (10 parts of concentrate/2 parts of water/3 parts of binder), applied to the foamed material and dried for at least 24 hours at room temperature. The wraps were applied.

| Copper penetration after a standing time of 12 months | | |
| --- | --- | --- |
| Round timber 1c: | average sapwood thickness: | approx. 32 mm |
| | average copper penetration: | approx. 12 mm |
| | At no point was the heart reached | |
| Round timber 2c: | average sapwood thickness: | approx. 43 mm |
| | average copper penetration: | approx. 10 mm |
| | At no point was the heart reached | |

EXAMPLE D (not according to the invention)

35% of copper acetate
65% of potassium fluoroborate

After the salt has been ground, it was made into a paste with water, acrylate dispersion (50% aqueous dispersion of a copolymer of n-butyl acrylate and styrene) as binder (10 parts of concentrate/2 parts of water/3 parts of binder), applied to the foamed material and dried for at least 24 hours at room temperature. The wraps were applied.

| Copper penetration after a standing time of 12 months | | |
| --- | --- | --- |
| Round timber 1d: | average sapwood thickness: | approx. 37 mm |
| | average copper penetration: | approx. 7 mm |
| | At no point was the heart reached | |
| Round timber 2d: | average sapwood thickness: | approx. 42 mm |
| | average copper penetration: | approx. 11 mm |
| | At no point was the heart reached | |

EXAMPLE E (not according to the invention)

41.55% by weight of demineralized water
10.70% by weight of sodium hydroxide
28.00% by weight of citric acid monohydrate
9.75% by weight of stabilized copper hydroxide
10.00% by weight of polybor ($Na_2B_8O_{13}$ [sic]×4 $H_2O$ [sic])
   Copper content of the concentrate: 6.1%
   Copper leaching in accordance with EN 84 (1 week fixing, concentration of solution 3.3%) is 94.5%.

EXAMPLE F (not according to the invention)

37.43% by weight of demineralized water
16.00% by weight of sodium hydroxide
26.82% by weight of malic acid
9.75% by weight of stabilized copper hydroxide
10.00% by weight of Polybor ($Na_2B_8O_{13}$ [sic]×4 $H_2O$ [Sic])
   Copper content of the concentrate: 6.1%
   Copper leaching in accordance with EN 84 (1 week fixing, concentration of solution 3.3%) is 67.5%.

EXAMPLE G (not according to the invention)

52.73% by weight of water
10.70% by weight of sodium hydroxide
26.82% by weight of malic acid
9.75% by weight of copper hydroxide
   Copper content of the concentrate: 6.1%
   Copper leaching in accordance with EN 84 (1 week fixing, concentration of solution 3.3%) is 71.5%.

EXAMPLE H (not according to the invention)

51.55% by weight of water
10.70% by weight of sodium hydroxide
28.00% by weight of citric acid monohydrate
9.75% by weight of copper hydroxide
   Copper content of the concentrate: 6.1%
   Copper leaching in accordance with EN 84 (1 week fixing, concentration of solution 3.3%) is 97.5%.

Examples according to the invention

EXAMPLE 1

31.25% by weight of monoethanolamine
30.93% by weight of water
15.63% by weight of malic acid
22.19% by weight of copper hydroxycarbonate
   Copper content of the concentrate: 12.5%.
   Copper leaching in accordance with EN 84 (1 week fixing, concentration of solution 1.6%) is 37.5%.

The concentrate was prepared by stirring, applied to foamed material and dried at room temperature for at least 24 hours. The wrap was applied.

| Copper penetration after a standing time of 12 months | | |
| --- | --- | --- |
| Round timber II 1: | average sapwood thickness: | approx. 36 mm |
| | average copper penetration: virtually identical to the sapwood zone Reaches the heart | |
| Round timber II 2: | average sapwood thickness: | approx. 32 mm |
| | average copper penetration: virtually identical to the sapwood zone Reaches the heart | |

EXAMPLE 2

35.00% by weight of monoethanolamine
30.31% by weight of water
12.50% by weight of citric acid monohydrate
22.19% by weight of copper hydroxycarbonate
   Copper content of the concentrate: 12.5%
   Copper leaching in accordance with EN 84 (1 week fixing, concentration of solution 1.6%) is 38.1%.

The concentrate was prepared by stirring, applied to foamed material and dried at room temperature for at least 24 hours. The wrap was applied.

| Copper penetration after a standing time of 12 months | | |
|---|---|---|
| Round timber II 1: | average sapwood thickness: | approx. 37 mm |
| | average copper penetration: virtually identical to the sapwood zone Reaches the heart | |
| Round timber II 2: | average sapwood thickness: | approx. 34 mm |
| | average copper penetration: virtually identical to the sapwood zone Reaches the heart | |

EXAMPLE 3

25.00% by weight of monoethanolamine
21.50% by weight of water
12.50% by weight of malic acid
16.00% by weight of stabilized copper hydroxide
25.00% by weight of boric acid
    Copper content of the concentrate: 10%
    Copper leaching in accordance with EN 84 (1 week fixing, concentration of solution 2%) is 35.3%.
    The concentrate was prepared by stirring, applied to foamed material and dried at room temperature for at least 24 hours. The wrap was applied.

| Copper penetration after a standing time of 12 months | | |
|---|---|---|
| Round timber II 1: | average sapwood thickness: | approx. 30 mm |
| | average copper penetration: virtually identical to the sapwood zone Reaches the heart | |
| Round timber II 2: | average sapwood thickness: | approx. 42 mm |
| | average copper penetration: virtually identical to the sapwood zone Reaches the heart | |

EXAMPLE 4

19.00% by weight of monoethanolamine
21.00% by weight of water
40.00% by weight of copper citrate (approx. 35% Cu)
20.00% by weight of boric acid
    Copper content of the concentrate: 14%
    Copper leaching in accordance with EN 84 (1 week fixing, concentration of solution 1.5%) is 44.0%.
    The concentrate was prepared by stirring, applied to foamed material and dried at room temperature for at least 24 hours. The wrap was applied.

| Copper penetration after a standing time of 12 months | | |
|---|---|---|
| Round timber II 1: | average sapwood thickness: | approx. 33 mm |
| | average copper penetration: virtually identical to the sapwood zone Reaches the heart | |
| Round timber II 2: | average sapwood thickness: | approx. 37 mm |

-continued

| Copper penetration after a standing time of 12 months | | |
|---|---|---|
| | average copper penetration: virtually identical to the sapwood zone Reaches the heart | |

EXAMPLE 5

25.00% by weight of monoethanolamine
21.50% by weight of water
12.50% by weight of citric acid monohydrate
16.00% by weight of stabilized copper hydroxide
25.00% by weight of boric acid
    Copper content of concentrate: 10%
    Copper leaching in accordance with EN 84 (1 week fixing, concentration of solution 2%) is 38.3%.
    The concentrate was prepared by stirring, applied to foamed material and dried at room temperature for at least 24 hours. The wrap was applied.

| Copper penetration after a standing time of 12 months | | |
|---|---|---|
| Round timber II 1: | average sapwood thickness: | approx. 31 mm |
| | average copper penetration: virtually identical to the sapwood zone Reaches the heart | |
| Round timber II 2: | average sapwood thickness: | approx. 39 mm |
| | average copper penetration: virtually identical to the sapwood zone Reaches the heart | |

EXAMPLE 6

28.00% by weight of monoethanolamine
20.50% by weight of water
10.00% by weight of citric acid monohydrate
16.00% by weight of stabilized copper hydroxide
25.00% by weight of sodium fluoride
    Copper content of the concentrate: 10%
    Copper leaching in accordance with EN 84 (1 week fixing, concentration of solution 2.0%) is 35.0%.
    The concentrate was prepared by stirring, applied to foamed material and dried at room temperature for at least 24 hours. The wrap was applied.

| Copper penetration after a standing time of 12 months | | |
|---|---|---|
| Round timber II 1: | average sapwood thickness: | approx. 35 mm |
| | average copper penetration: virtually identical to the sapwood zone Reaches the heart | |
| Round timber II 2: | average sapwood thickness: | approx. 40 mm |
| | average copper penetration: virtually identical to the sapwood zone Reaches the heart | |

EXAMPLE 7

8.80% by weight of monoethanolamine
7.80% by weight of water 18.60% by weight of copper citrate (approx. 35% Cu)
9.00% by weight of boric acid
22.50% by weight of sodium fluoride
33.30% by weight of polyvinyl chloride powder (Vinnolit P 4472, by Vinnolit)/bis(2-ethylhexyl) phthalate premix (mixing ratio: approx. 4:5)

A paste was prepared by stirring, applied to foamed material and dried for at least 15 minutes in the continuous oven at 130° C. The wrap was applied.

Copper penetration after a standing time of 12 months

| | | |
|---|---|---|
| Round timber II 1: | average sapwood thickness: | approx. 40 mm |
| | average copper penetration: virtually identical to the sapwood zone Reaches the heart | |
| Round timber II 2: | average sapwood thickness: | approx. 39 mm |
| | average copper penetration: virtually identical to the sapwood zone Reaches the heart | |

Further examples with good diffusion properties

EXAMPLE 8

26.50% by weight of monoethanolamine
9.50% by weight of water
23.00% by weight of 57% strength glycolic acid (commercially available)
16.00% by weight of stabilized copper hydroxide
25.00% by weight of boric acid

EXAMPLE 9

25.00% by weight of monoethanolamine
22.00% by weight of 80% strength lactic acid (commercially available)
12.00% by weight of water
16.00% by weight of stabilized copper hydroxide
25.00% by weight of boric acid

EXAMPLE 10

25.00% by weight of monoethanolamine
24.75% by weight of water
12.50% by weight of tartaric acid
17.75% by weight of copper hydroxycarbonate
20.00% by weight of Polybor ($Na_2B_8O_{13}$ [sic]×4 $H_2O$)

We claim:

1. A wood preservative for the supplemental protection of wood, consisting essentially of one or more copper compounds, one or more alkanolmonoamines and one or more complexing organic carboxylic acids or ammonium or alkali metal salts of said complexing organic carboxylic acids.

2. A wood preservative as claimed in claim 1, consisting essentially of one or more copper compounds selected from the group consisting of copper sulfate, copper acetate, copper citrate, copper naphthenate, copper hydroxide, copper hydroxycarbonate, copper oxychloride, copper oxide, copper borate, copper fluoride, copper fluoroborate and bis(N-cyclohexyldiazeniumdioxy)copper.

3. A wood preservative as claimed in claim 1, consisting essentially of one or more alkanolmonoamines selected from the group consisting of monoethanolamine, diethanolamine, triethanolamine, isopropanolamine and methyl ethanolamine.

4. A wood preservative as claimed in claim 3, consisting essentially of one or more alkanolmonoamines selected from the group consisting of monoethanolamine, diethanolamine and triethanolamine.

5. A wood preservative as claimed in claim 1, wherein said one or more alkanolmonoamines includes monoethanolamine.

6. A wood preservative as claimed in claim 2, consisting essentially of one or more complexing organic carboxylic acids selected from the groups consisting of hydroxycarboxylic acids, aminocarboxylic acids, nitrogen-containing polycarboxylic acids and ammonium or alkali metal salts of said complexing organic carboxylic acids.

7. A wood preservative as claimed in claim 6, consisting essentially of one or more complexing organic carboxylic acids, selected from the group consisting of grycolic acid, lactic acid, malic acid, tartaric acid, citric acid, nitrilotriacetic acid, ethylenediaminetetraacetic acid, diethylenetriamine-pentaacetic acid, propylenediaminetetraacetic acid, hydroxyethytethylenediaminetriacetic acid, β-alaninediacetic acid, sarcosine, glycine and ammonium and alkali metal salts of said complexing organic carboxylic acids.

8. A wood preservative as claimed in claim 1, additionally comprising one or more inorganic fungicides selected from the group consisting of boron compounds, fluorides, fluoroborates, fluorophosphates and difluorophosphates.

9. A wood preservative as claimed in claim 8, additionally comprising one or more inorganic fungicides selected from the group consisting of alkali metal borates, aminoborates, boric acid, boric esters, $B_2O_3$, alkali metal fluorides, alkali metal bifluorides, silicon fluorides, ammonium fluorides, ammonium hydrogen fluorides, fluoroborates, fluorophosphates and difluorophosphates.

10. A wood preservative as claimed in claim 1, additionally comprising one or more auxiliaries selected from the group consisting of water, binders, paste formers, organic and inorganic bases, aliphatic carboxylic acids, plasticizers, fillers, wetters and thickeners.

11. A wood preservative as claimed in claim 1, consisting essentially of

2–50% by weight of a copper compound,
2–60% by weight of an alkanolmonoamine,
1–65% by weight of a complexing organic carboxylic acid or an ammonium or alkali metal salt thereof,
0–50% by weight of an inorganic fungicide,
0–25% by weight of an alkali metal salt of N-cyclohexyldiazenium dioxide,
0–25% by weight of an auxiliary,
0–50% by weight of water,
the total of all components being 100% by weight.

12. A wrap for the supplemental protection of wood, comprising a support and a wood preservative as claimed in claim 1.

13. A method for the supplemental protection of wood by treating said wood with a fungicidally effective amount of the wood preservative as claimed in claim 1.

14. The method of claim 13, in which the treatment is carried out by the wrap method, the injection inoculation method, the drilled hole method or the paste method.

15. A method for the supplemental protection of wood which consists essentially of treating said wood with the wood preservative as claimed in claim 2.

16. A method for the supplemental protection of wood which consists essentially of treating said wood with a wood preservative as claimed in claim 8.

17. A method for the supplemental protection of wood which consists essentially of treating said wood with a wood preservative as claimed in claim 10.

18. A method for the supplemental protection of wood consisting essentially of applying to said wood a wood preservative as claimed in claim 11.

19. A method for the supplemental protection of wood consisting essentially of wrapping said wood with a wrap as claimed in claim 12.

\* \* \* \* \*